United States Patent [19]
Rosenauer

[11] Patent Number: 5,641,456
[45] Date of Patent: Jun. 24, 1997

[54] APPARATUS AND METHOD FOR CLEANING

[75] Inventor: Charles E. Rosenauer, Louisville, Ky.

[73] Assignee: Marco Equipment Distributors, Inc., Louisville, Ky.

[21] Appl. No.: 527,836

[22] Filed: Sep. 13, 1995

[51] Int. Cl.⁶ .................................................. A61L 2/18
[52] U.S. Cl. ........................... 422/29; 422/28; 134/22.1; 134/22.11
[58] Field of Search ................... 134/22.1, 22.11, 134/22.12, 28, 29; 422/24, 14, 28, 29

[56] References Cited

U.S. PATENT DOCUMENTS

| | | |
|---|---|---|
| 3,546,114 | 12/1970 | Dietz et al. ............................... 210/760 |
| 3,871,913 | 3/1975 | Shaldon ................................. 134/22.18 |
| 4,158,034 | 6/1979 | Riede et al. ........................... 134/22.12 |
| 4,166,031 | 8/1979 | Hardy .................................... 134/22.18 |
| 4,201,664 | 5/1980 | Hekal ....................................... 508/111 |
| 4,444,596 | 4/1984 | Gortz et al. ........................... 134/22.12 |
| 4,444,597 | 4/1984 | Gprtz et al. ........................... 134/22.12 |
| 4,619,763 | 10/1986 | O'Brien .................................... 210/177 |
| 4,690,772 | 9/1987 | Tell et al. ................................ 252/106 |
| 4,898,679 | 2/1990 | Siegel et al. ............................ 210/752 |
| 5,078,967 | 1/1992 | Riera Aixala ........................... 134/22.1 |
| 5,173,125 | 12/1992 | Felding .................................. 134/22.11 |
| 5,178,830 | 1/1993 | Riera Aixala ........................... 134/22.1 |
| 5,192,459 | 3/1993 | Tell et al. ................................ 252/106 |
| 5,336,165 | 8/1994 | Twardowski ................................ 604/5 |
| 5,368,815 | 11/1994 | Kasting, Jr. et al. ....................... 422/3 |
| 5,370,740 | 12/1994 | Chao et al. ................................. 134/1 |
| 5,397,397 | 3/1995 | Awad ......................................... 134/1 |
| 5,409,612 | 4/1995 | Maltais et al. ........................... 210/636 |

*Primary Examiner*—Jill Warden
*Assistant Examiner*—Alexander Markoff
*Attorney, Agent, or Firm*—Wheat, Camoriano, Smith & Beres, PLC

[57] ABSTRACT

An apparatus and a method for cleaning a device using ozonated water.

3 Claims, 2 Drawing Sheets

5,641,456

APPARATUS AND METHOD FOR CLEANING

BACKGROUND OF THE INVENTION

The present invention relates to an apparatus and method for cleaning and disinfecting a machine or device. For example, in the past, the standard method for cleaning a dialysis machine entailed delivering a solution of cleaning chemicals, such as an acid or base solution, a detergent, or an enzyme, into the dialysis machine and running the cleaning solution through the dialysis machine until any contaminants, such as blood, were removed from the machine, and all pathogens were killed. To prevent any traces of the cleaning chemical from being left in the dialysis machine, which would contaminate the next patient's blood, the dialysis machine had to be rinsed several times with water before the next dialysis procedure could be performed.

The standard method of cleaning a dialysis machine, while satisfactory to the extent of producing a clean dialysis machine, has a number of disadvantages associated with it. One significant problem is the amount of time required to complete one cleaning procedure, which is approximately an hour. A technician must be present to operate the process, so this process is expensive in terms of labor costs. Also, the chemicals are expensive, and large amounts of water are used, which is also expensive, both in terms of the cost of the water and in terms of the cost of treating the water which leaves the machine. Also, since the dialysis machine cannot be used while it is being cleaned, a long cleaning cycle severely limits the amount of time a machine can be used during a day, thereby limiting the number of patients that can be served and the income that can be generated from using the machine.

Another problem occurring with the standard method of cleaning a dialysis machine is the disposal of the cleaning solution after the cleaning process is completed. The used cleaning solution is often considered to be a toxic chemical requiring special disposal. Another problem with the standard method of cleaning a dialysis machine is that, if any traces of the cleaning chemicals are left in the machine, they can end up in the next patient's blood stream, perhaps harming the patient.

SUMMARY OF THE INVENTION

It is an object of the present invention to provide a fast method of cleaning a machine or device in order to reduce the "down time" of the machine or device and to reduce the labor costs associated with cleaning the machine or device.

It is a further object of the present invention to provide a method of cleaning a machine or device without using solutions of toxic chemicals.

It is a still further object of the present invention to provide a cleaning method using a cleaning solution which does not leave any residue of a toxic chemical on a machine or device being cleaned.

It is another object of the present invention to provide a cleaning method that does not require extensive use of water for rinsing a machine or device after the machine or device has been cleaned.

It is yet another object of the present invention to provide a cleaning method that does not require extensive purification of the rinse water after a machine or device has been rinsed.

Accordingly, the present invention provides an apparatus and method for fulfilling the above objectives.

The present invention uses ozonated water as a cleaning agent instead of using cleaning solutions. The ozonated water disinfects and cleans quickly and without leaving any residue, because the ozone quickly converts to oxygen and goes into the atmosphere. Thus, little or no rinsing is required after using the ozonated water to clean a machine or device.

While the use of ozone to purify water is well known, ozonated water has not been used in the past to disinfect a machine or a device.

DETAILED DESCRIPTION OF THE PREFERRED EMBODIMENT

Figure 1:
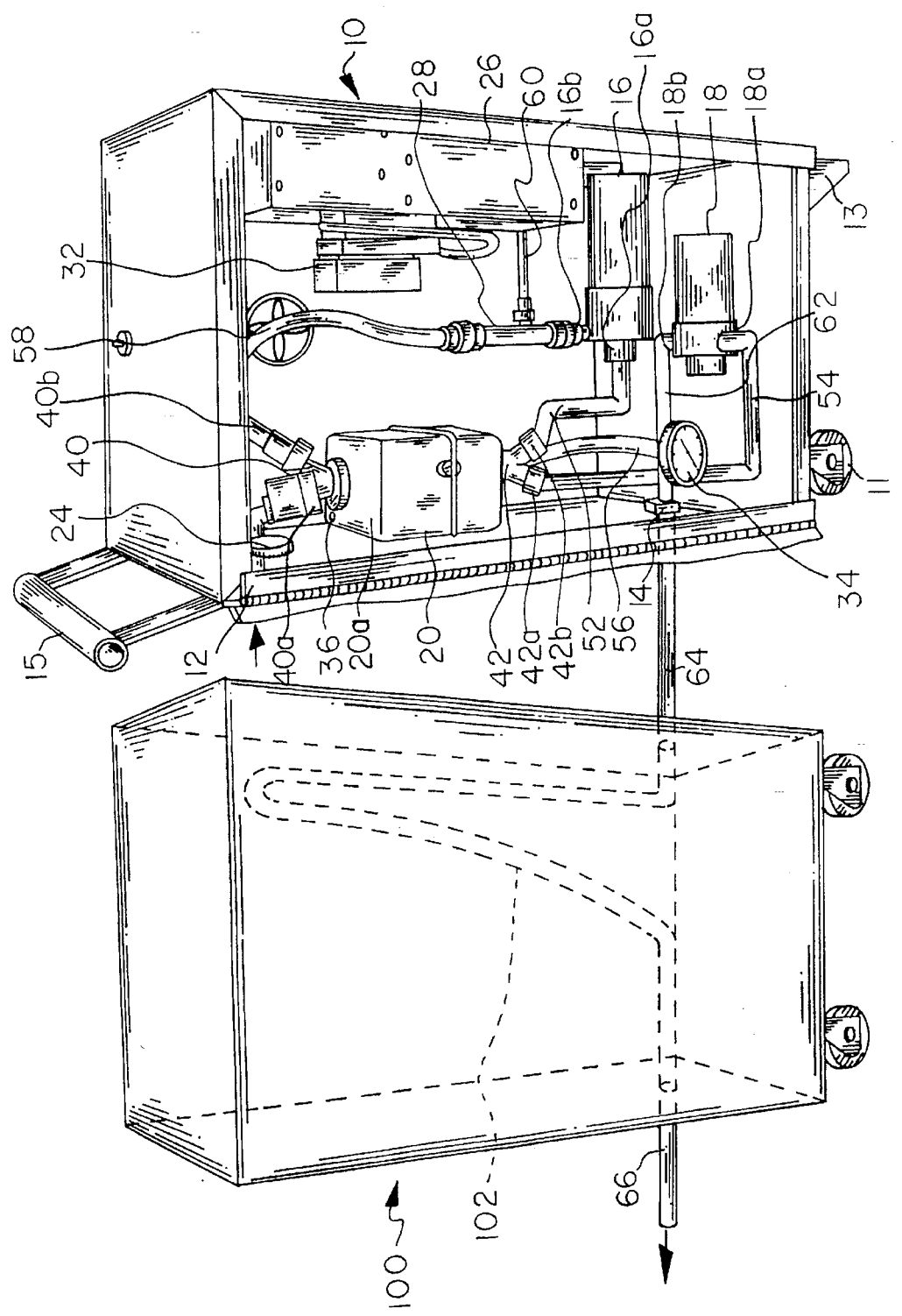
FIG. 1 is a side view, with the door open and partially broken away, of an embodiment of the present invention being used to clean a dialysis machine.
Figure 3:
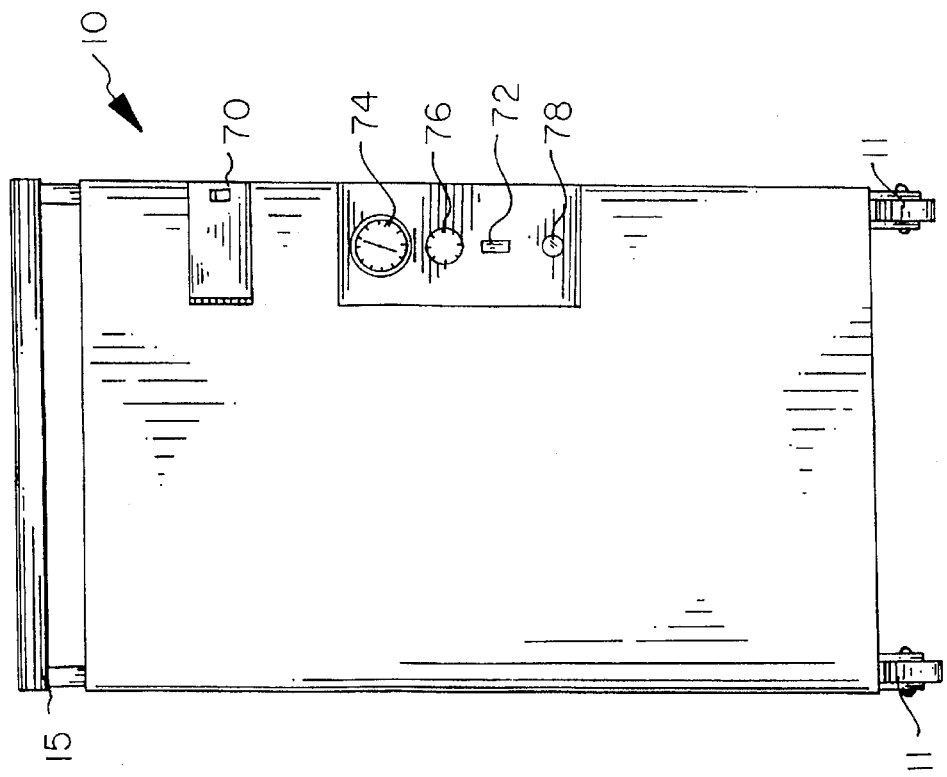
FIG. 3 is a back view of the embodiment of FIG. 1.
Figure 2:
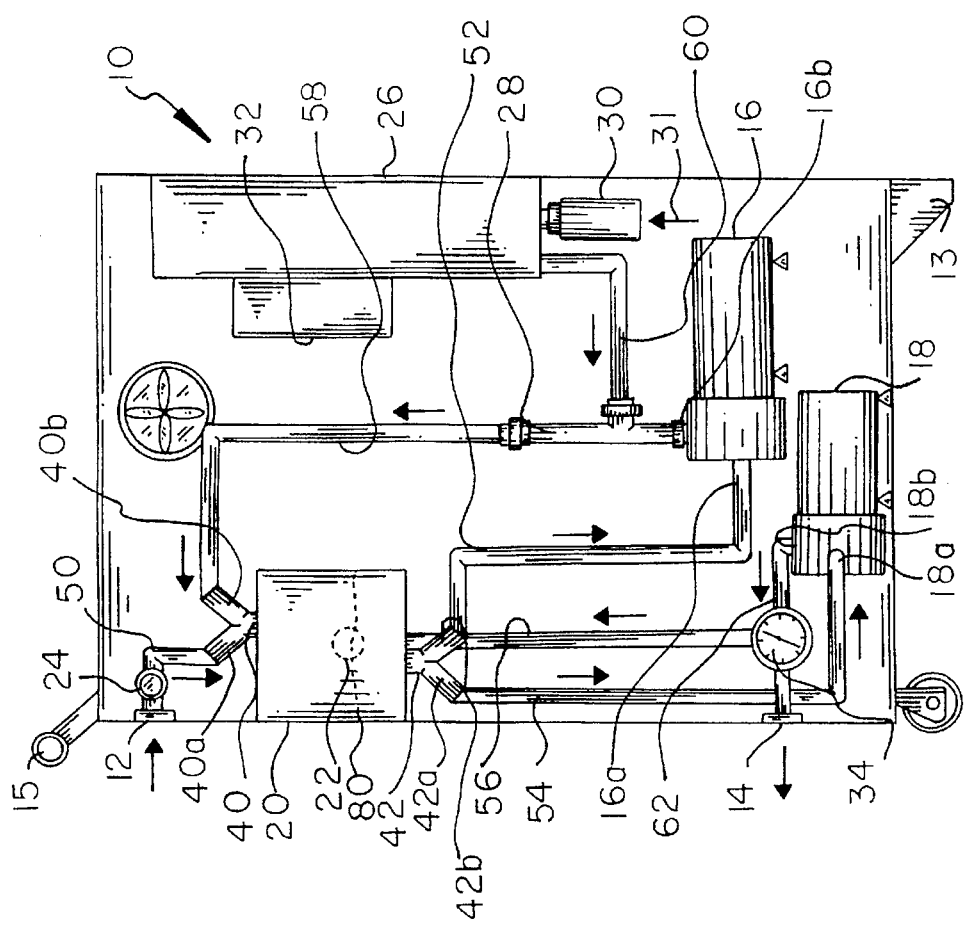
FIG. 2 is a schematic side view of the embodiment of FIG. 1.

The cleaning apparatus 10 of the present invention is shown in FIGS. 1–3. The apparatus 10 has a water inlet 12, a tank 20 for holding water, a first pump 16 having an inlet side 16a and an outlet side 16b, a second pump 18 having an inlet side 18a and an outlet side 18b, an ozone generator 26, and a water outlet 14. A float 22 is located inside the tank 20, buoyantly riding atop a water level 80, which is shown in phantom in FIG. 2. The tank 20 is vented to the atmosphere by an opening 36 in the top face 20a of the tank 20, as seen in FIG. 1. A first Y-shaped water conduit 40 is mounted to the top of the tank 20. A first leg 40a of the conduit 40 is connected to the water inlet 12 through a pipeline 50 equipped with a solenoid valve 24, while a second leg 40b of the conduit 40 is connected to a Venturi tube 28 through a line 58. A second Y-shaped water conduit 42 is mounted to the bottom of the tank 20. A first leg 42a of the conduit 42 is connected to the inlet side 18a of the second pump 18 by a line 54, while a second leg 42b of the conduit 42 is connected to the inlet side 16a of the first pump 16 by a line 52. The ozone generator 26 has an air filter 30 and a pressure switch 32 and is connected to the Venturi tube 28 by a line 60. The Venturi tube 28 is also connected to the outlet side 16b of the first pump 16. The outlet side 18b of the second pump 18 is connected to the water outlet 14 by a line 62 equipped with a pressure gauge/bypass valve 34. There is a bypass path from the line 62 through the pressure gauge/bypass valve 34 through bypass line 56 back to the tank 20. As best seen in FIG. 3, the cleaning apparatus 10 includes an electric box 70, an on/off switch 72, a timer 74, a counter 76, and a red light 78. The apparatus 10 is also equipped with rear wheels 11, front legs 13, and a handle 15. The path from the leg 42b at the bottom of the tank 20 through the line 52, through the pump 16, through the Venturi tube 28, through the line 58, and back into the tank 20 is referred to as an ozonation loop, because the water from the tank 20 is ozonated as it passes through this loop.

The operation of the cleaning apparatus 10 can best be understood by reference to FIG. 2. Before the apparatus 10 is used, the tank 20 is supplied with water from a water supply (not shown). For best results, purified water, such as from a reverse osmosis machine, should be used. After the water supply is connected to the inlet 12 by some means, such as a hose or a pipe, and the water supply is turned on, water from the water supply will enter the apparatus 10 at the inlet 12 and will flow through the line 50 and leg 40a into the tank 20. The water will flow through the tank 20 until it fills lines 52, 54, and 56, and then the water will begin filling the tank 20. Then, the water level 80 in the tank will rise until the float 22 reaches a predetermined level, at which point the float 22 activates the solenoid valve 24 at the water inlet 12. The solenoid valve 24 then closes off line 50 and stops the flow of water into the tank 20.

When an operator turns on the apparatus 10 by flipping the on/off switch 72, the first pump 16 and the ozone generator 26 are turned on. The first pump 16 begins pumping water from the tank 20 through the line 52 through the Venturi tube 28, where the water is mixed with ozonated air from the ozone generator 26, through the line 58, and back into the tank 20. At the same time, the ozone generator 26 begins to take in air through the air filter 30, as indicated by arrow 31. The air is filtered to remove contaminants, is dehumidified, and then the ozone generator 26 converts the oxygen in the air to ozone by passing an electric arc through the air, in a known process. Ozone exits the ozone generator 26 through the line 60 and enters the Venturi tube 28. The Venturi tube 28 provides a reduced diameter in the water flow path, which creates a vacuum that pulls the ozonated air into the water flow path and mixes the water and the ozonated air in a well-known manner. Thus, because the first pump 16 is continuously recirculating water between the tank 20 and the ozone generator 26, the water in the tank 20 becomes ozonated.

When the pressure switch 32 associated with the ozone generator 26 detects a pressure change which indicates that ozone is being drawn into the Venturi tube 28, the pressure switch 32 activates the second pump 18. The second pump 18 begins to take water from the tank 20 through the line 54 and to pump this water to the outlet 14 via the line 62. This causes the water level 80 in the tank 20 to go down, which causes the float 22 to open the solenoid valve 24, thus allowing water from the water supply to flow into the tank 20, thus keeping an adequate supply of water coming to the apparatus 10. It will be appreciated that the water being pumped to the outlet 14 by the second pump 18 will not be ozonated at first, since the water standing in the line 54 will be pumped out first, but the water being pumped to the outlet 14 will be ozonated water once the pump 18 begins to receive water from the tank 20, since ozonated water has now been pumped into the tank 20.

The pressure gauge 34 monitors the pressure of the water flowing through the line 62. To ensure that the pressure of the water exiting outlet 14 does not exceed rated levels, the pressure gauge 34 includes a bypass valve which will be opened whenever the water in the line 62 reaches a set pressure. When opened, the bypass valve in the gauge/valve 34 sends some of the water flowing through the line 62 into the bypass line 56, and back into the tank 20.

It has been found through testing that the use of two separate pumps is preferable to the use of a single pump, because a single pump was unable to maintain the proper outlet pressure for water passing through the outlet 14. Also, by using one pump solely for ozonating the water in the tank 20, the embodiment described herein ensures constant circulation of ozonated water to the tank 20.

By reference to FIG. 1, a method for the use of the preferred embodiment of the cleaning apparatus 10 to clean a device, such as the dialysis machine 100, can be understood. An operator moves the apparatus 10 into the desired position by pushing down on the handle 15 and tilting the cleaning apparatus 10 backwards so that the weight of the apparatus 10 is taken off of the legs 13 and placed entirely upon the wheels 11, which makes the apparatus 10 easy to roll into place. When the apparatus 10 is in the desired position, the operator merely tilts the apparatus 10 forward until the legs 13 contact the ground. A hose 64 is used to carry ozonated water from the outlet 14 of the apparatus 10 into the dialysis machine 100. The ozonated water flows along an enclosed liquid pathway 102, which is shown in phantom, inside the dialysis machine 100, removing contaminants and disinfecting the interior of the pathway 102. The ozonated water and associated impurities from the dialysis machine 100 exit through a liquid outlet 66 and go to a drain (not shown).

Since the ozone in the enclosed pathway is protected from contact with the atmosphere, the ozone gas tends to stay in solution in the water during the time the ozonated water is being pumped through the enclosed pathway 102. However, when the ozonated water exits the outlet 66 and comes into contact with the atmosphere, any remaining ozone in the ozonated water is quickly converted to oxygen, which dissipates into the atmosphere. Since no refrigeration or heating devices are shown, it can be seen that no artificial chilling or heating of the water is done from the time the water enters the tank until it leaves the dialysis machine. After turning off the cleaning apparatus 10 and removing the hose 64 from the inlet of the dialysis machine 100, any ozone remaining in the dialysis machine 100 dissipates to the atmosphere, leaving no contaminants in the dialysis machine 100.

The dialysis machine 100 is then ready for use, with no further cleaning or rinsing being necessary. However, while it will usually be unnecessary, once the flow of ozonated water to the dialysis machine 100 has stopped, it can be followed by a flow of clean rinse water to flush out the dialysis machine 100. Even if the dialysis machine 100 is rinsed with fresh water, a much smaller amount of water will be necessary than the amount of water needed to rinse a chemical cleaning solution out of the dialysis machine 100, thereby saving the expense of the extra water and the increased "down time".

The operation of the control system of the cleaning apparatus 10 is as follows: the on/off switch 72 turns on the electric power supply to the electric box 70, and turns on the ozone generator 26 and the first pump 16. The timer 74 sets the desired amount of cleaning time, and the counter 76 lets an operator of the dialysis machine 100 know how much time is left in the cleaning cycle. The red light 78 lights up whenever the apparatus 10 is in use, letting any persons desiring to use the cleaning machine 10 know that they will have to wait before using it. The float 22 in the tank 20 controls the solenoid valve 24, ensuring that there will be enough water inside the tank 20. The pressure switch 32 of the ozone generator 26 turns on the second pump 18 upon detecting a pressure change which indicates that ozone is being drawn into the Venturi tube 28.

Thus, an apparatus and a method for using ozonated water to clean and disinfect a machine or a device has been described. The use of the present inventive method, especially when performed by use of the present inventive apparatus, provides a quick way of cleaning and disinfecting a machine such as a dialysis machine, thus reducing "down time" and allowing the machine to be used more often. This quick cleaning is accomplished without the use of any toxic chemicals and leaves very little, if any, residue on the machine. Moreover, since cleaning chemicals can be quite expensive to buy and to dispose of properly, the present inventive method provides a much more economical way of cleaning a machine. It should also be understood that the present inventive method of cleaning a machine or device using ozonated water, as described herein, is fully applicable for cleaning other machines and devices having an enclosed liquid pathway with an inlet and an outlet.

It will be obvious to those skilled in the art that modifications may be made to the embodiment described above without departing from the scope of the present invention.

What is claimed is:

1. A method for cleaning a dialysis machine having an enclosed liquid pathway and defining an inlet and an outlet, comprising the steps of:

(a) introducing purified water into a tank;

(b) using a first pump to circulate the purified water from said tank through an ozonation loop, in which ozone is introduced into the purified water thereby producing ozonated purified water which is returned to said tank;

(c) continuing to use the first pump to circulate the ozonated purified water through said ozonation loop;

(d) using a second pump to pump the ozonated purified water from said tank to the inlet of the enclosed liquid pathway while said first pump continues circulating the ozonated purified water through the ozonation loop;

(e) passing said ozonated purified water through the enclosed liquid pathway to clean and disinfect the dialysis machine; and (f) passing said ozonated purified water out of said dialysis machine through the outlet.

2. A method for cleaning a dialysis machine as recited in claim 1, and further comprising the steps of:

using an ozone generator to make ozone from oxygen in air; and passing said purified water through a Venturi tube in said ozonation loop, wherein ozone is introduced into said purified water as it passes through said Venturi tube.

3. A method for cleaning a dialysis machine as recited in claim 1, and further comprising the steps of;

stopping passing said purified ozonated water from said tank into said inlet: and passing rinse water into said inlet, through said enclosed liquid pathway, and out said outlet, to rinse said dialysis machine.

* * * * *